United States Patent

Naito

[11] Patent Number: 6,054,586

[45] Date of Patent: Apr. 25, 2000

[54] PROCESS FOR THE PREPARATION OF 4-METHYLENEPIPERIDINE

[75] Inventor: Takanobu Naito, Kyoto, Japan

[73] Assignee: Kaken Pharmaceutical Co., Ltd., Tokyo, Japan

[21] Appl. No.: 09/043,696

[22] PCT Filed: Sep. 26, 1996

[86] PCT No.: PCT/JP96/02810

§ 371 Date: Mar. 26, 1998

§ 102(e) Date: Mar. 26, 1998

[87] PCT Pub. No.: WO97/11939

PCT Pub. Date: Apr. 3, 1997

[30] Foreign Application Priority Data

Sep. 28, 1995 [JP] Japan ................................ 7-251637

[51] Int. Cl.$^7$ ..................... C07D 211/06; C07D 211/60
[52] U.S. Cl. ................................... 546/226; 546/245
[58] Field of Search ................... 546/248, 184, 546/226, 245

[56] References Cited

U.S. PATENT DOCUMENTS

| 4,243,807 | 1/1981 | Friebe et al. ........................ 546/232 |
| 5,298,503 | 3/1994 | Peglion et al. ........................ 546/141 |
| 5,620,994 | 4/1997 | Naito et al. ........................ 514/326 |

FOREIGN PATENT DOCUMENTS

| 47-6514 | 4/1972 | Japan . |
| 55-113715 | 9/1980 | Japan ........................ C07D 211/12 |
| 4-112868 | 4/1992 | Japan ........................ C07D 207/08 |
| 5-208973 | 8/1993 | Japan ........................ C07D 401/12 |

OTHER PUBLICATIONS

Bingwei V. Yang et al. Mild and Selective Debenzylation of Tertiary Amines Using α–Chloroethyl Chloroformate:, Synlett, 1993, vol. 3, pp. 195–196.

International Search Report.

P. Brenneisen et al., Helvetica Chimica Acta, 48(1), 146–156 (1965).

Derwent Abstract WPI No. 92–173201/199221 of JP 4–112868.

Primary Examiner—John Kight
Assistant Examiner—Raymond Covington
Attorney, Agent, or Firm—Sughrue, Mion, Zinn, Macpeak & Seas, PLLC

[57] ABSTRACT

A process for preparing 4-methylenepiperidine having a formula (VII):

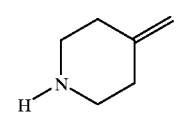

(VII)

which comprises reacting an isonipecotate having a formula (I):

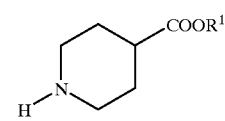

(I)

wherein $R^1$ is methyl group or ethyl group, with an acylating agent having a formula (II): $R^2X$ or a formula (II'): $(R^2)_2O$ wherein $R^2$ is benzoyl group or acetyl group and X is chlorine atom or bromine atom, in the presence or the absence of a base, reducing the resulting ester having a formula (III):

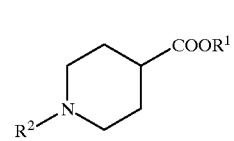

(III)

wherein $R^1$ and $R^2$ are the same as defined above, with sodium borohydride or lithium borohydride in an organic solvent containing methanol, reacting the resulting alcohol with a halogenating agent without any solvent or in an organic solvent in the presence or the absence of a base, reacting the resulting halide with a dehydrohalogenating agent in an organic solvent and hydrolyzing the resulting methylene compound having a formula (VI):

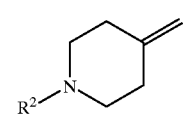

(VI)

wherein $R^2$ is the same as defined above, with a strong alkaline in water or an organic solvent containing water.

7 Claims, No Drawings

PROCESS FOR THE PREPARATION OF 4-METHYLENEPIPERIDINE

TECHNICAL FIELDS

The present invention relates to a process for preparing 4-methylenepiperidine which is an intermediate for the synthesis of a compound having a formula (VIII):

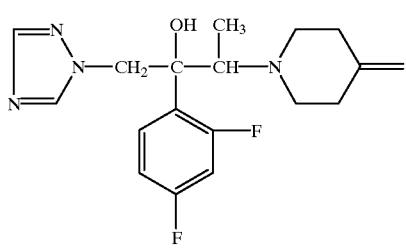
(VIII)

(a compound described in Example 1 in the published International Application No. WO 94/26734(1994)) known to be useful as a fungicide.

BACKGROUND ART

As a process for synthesizing 4-methylenepiperidine, there have been known the method wherein an aqueous solution of 4-bromoquinuclidine is heated (P. Brenneisen et al., Helv. Chim. Acta, 48(1), 146–156(1965)) and the method wherein N-benzyl-4-piperidone is reacted with a Wittig reagent and then debenzylation is carried out to obtain 4-methylenepiperidine (M. Mimura et al., Chem. Pharm. Bull., 41(11), 1971–1986(1993)). However, by either of these methods, it is difficult to manufacture a large amount of 4-methylenepiperidine at low cost because of the difficulty of obtaining the starting material or the use of an expensive reagent such as the Wittig reagent.

The object of the present invention is to provide a process for preparing 4-methylenepiperidine efficiently in short process from a cheap starting material which is obtainable at large amount.

DISCLOSURE OF THE INVENTION

As the result of the continuous effort and detailed investigation of the present inventors to achieve the above-mentioned object, they have found a process for preparing 4-methylenepiperidine at low cost wherein a starting material is an isonipecotate which is easily obtainable at low price.

The present invention relates to a process for preparing a methylene compound having a formula (VI):

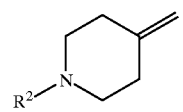
(VI)

wherein $R^2$ is benzoyl group or acetyl group, which comprises reacting a halide having a formula (V):

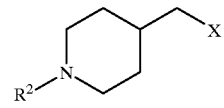
(V)

wherein X is chlorine atom or bromine atom and $R^2$ is the same as defined above, with a dehydrohalogenating agent in an organic solvent, a process for preparing an alcohol having a formula (IV):

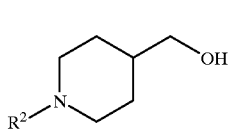
(IV)

wherein $R^2$ is benzoyl group or acetyl group, which comprises reducing an ester having a formula (III):

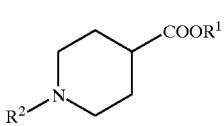
(III)

wherein $R^1$ is methyl group or ethyl group and R2 is the same as defined above, with sodium borohydride or lithium borohydride in an organic solvent containing methanol, a process for preparing a halide having a formula (V):

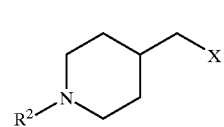
(V)

wherein X is chlorine atom or bromine atom and $R^2$ is benzoyl group or acetyl group, which comprises reacting an alcohol having a formula (IV):

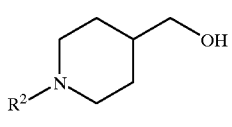
(IV)

wherein $R^2$ is the same as defined above, with a halogenating agent without any solvent or in an organic solvent in the presence or the absence of a base, a process for preparing a methylene compound having a formula (VI):

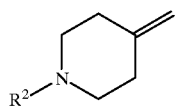

(VI)

wherein $R^2$ is benzoyl group or acetyl group, which comprises reducing an ester having a formula (III):

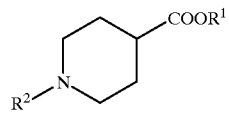

(III)

wherein $R^1$ is methyl group or ethyl group and $R^2$ is the same as defined above, with sodium borohydride or lithium borohydride in an organic solvent containing methanol, reacting a resulting alcohol having a formula (IV):

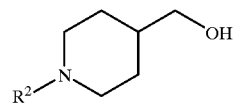

(IV)

wherein $R^2$ is the same as defined above, with a halogenating agent without any solvent or in an organic solvent in the presence or the absence of a base and reacting a resulting halide having a formula (V):

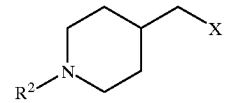

(V)

wherein X is chlorine atom or bromine atom and $R^2$ is the same as defined above, with a dehydrohalogenating agent in an organic solvent, a process for preparing an ester having a formula (III):

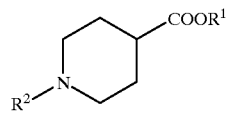

(III)

wherein $R^1$ is methyl group or ethyl group and $R^2$ is benzoyl group or acetyl group, which comprises reacting an isonipecotate having a formula (I):

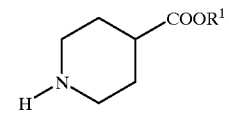

(I)

wherein $R^1$ is the same as defined above, with an acylating agent having a formula (II): $R^2X$ or a formula (II'): $(R^2)_2O$ wherein $R^2$ is the same as defined above and X is chlorine atom or bromine atom, in the presence or the absence of a base, a process for preparing 4-methylenepiperidine having a formula (VII):

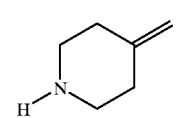

(VII)

which comprises hydrolyzing a methylene compound having a formula (VI):

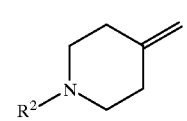

(VI)

wherein $R^2$ is benzoyl group or acetyl group, with a strong alkaline in water or an organic solvent containing water, and a process for preparing 4-methylenepiperidine having a formula (VII):

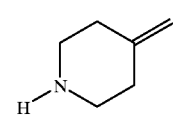

(VII)

which comprises reacting an isonipecotiate having a formula (I):

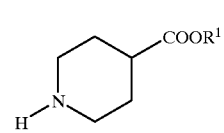

(I)

wherein $R^1$ is methyl group or ethyl group, with an acylating agent having a formula (II): $R^2X$ or a formula (II'): $(R^2)_2O$ wherein $R^2$ is benzoyl group or acetyl group and X is chlorine atom or bromine atom, in the presence or the absence of a base, reducing a resulting ester having a formula (III):

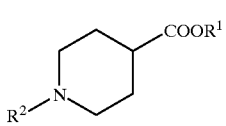

(III)

wherein $R^1$ and $R^2$ are the same as defined above, with sodium borohydride or lithium borohydride in an organic solvent containing methanol, reacting a resulting alcohol having a formula (IV):

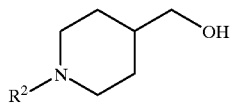

(IV)

wherein R² is the same as defined above, with a halogenating agent without any solvent or in an organic solvent in the presence or the absence of a base, reacting a resulting halide having a formula (V):

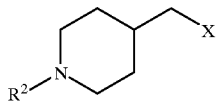

(V)

wherein X and R² are the same as defined above, with a dehydrohalogenating agent in an organic solvent and hydrolyzing a resulting methylene compound having a formula (VI):

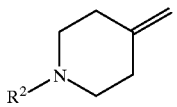

(VI)

wherein R² is the same as defined above, with a strong alkaline in water or an organic solvent containing water.

BEST MODE FOR CARRYING OUT THE INVENTION

The processes of the present invention are explained below according to the stages. Each stage in the present invention can be carried out using the starting compound at any amount ranging from the g-level to the 100 kg-level, and the amount of the solvent can be determined according to the amount of the starting compound to be used.

An isonipecotate having the formula (I):

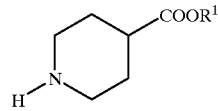

(I)

wherein R¹ is methyl group or ethyl group, is reacted with an acylating agent having the formula (II): R²X or the formula (II'): (R²)₂O, wherein R² is benzoyl group or acetyl group and X is chlorine atom or bromine atom, in the presence or the absence of a base to obtain an ester having the formula (III):

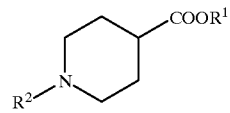

(III)

wherein R¹ and R² are the same as defined above.

As the isonipecotate, a commercially available one can be used and it is available from, for instance, TOKYO KASEI KOGYO Co., Ltd. Preferable acylating agents (II) used in the reaction are benzoyl chloride and acetyl chloride as an acyl halide and acetic anhydride and benzoic anhydride as an acid anhydride. Particularly, benzoyl chloride is preferable from the viewpoint of that it is obtainable at low price and it is easy to purify the produced material. The amount of the acylating agent (II) is from 1 to 2 molar equivalents, preferably from 1 to molar equivalents, based on the isonipecotate (I).

In the case of using the base, there can be used an organic base such as pyridine, triethylamine or morpholine or an inorganic base such as sodium hydroxide, potassium hydroxide, sodium carbonate, potassium carbonate or sodium hydrogencarbonate. The amount of the base is from the same amount to the excessive amount, preferably from 1 to 1.5 molar equivalents, based on the isonipecotate (I).

The reaction is carried out using or not using a solvent. Examples of the solvent are hydrocarbons such as toluene, xylene, benzene and hexane, esters such as ethyl acetate and butyl acetate, amides such as N,N-dimethylformamide and N,N-dimethylacetoamide, ethers such as dioxane, tetrahydrofuran and diisopropyl ether, halogenated hydrocarbons such as dichloromethane, 1,2-dichloroethane and chloroform, a mixture of at least two kinds of the above-mentioned solvents, and a mixed solvent of water and at least one kind of the above-mentioned solvents.

The reaction is carried out at the reaction temperature of from −20° to 100° C., with cooling, at room temperature or, if necessary, with heating. The reaction time is from 1 to 24 hours. The reaction can be carried out under any pressure and, usually, is carried out at atmospheric pressure. The produced compound may be purified according to the usual method.

Then, the ester (III) is reduced with sodium borohydride or lithium borohydride in an organic solvent containing methanol to obtain an alcohol having the formula (IV):

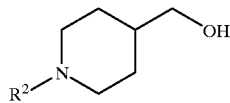

(IV)

wherein R² is the same as defined above.

The amount of sodium borohydride or lithium borohydride is from 1 to 2 molar equivalents based on the ester (III). The amount of methanol is from 1 to 3 molar equivalents, preferably 3 molar equivalents based on sodium borohydride or lithium borohydride. Examples of the organic solvent used are ethers such as dioxane and tetrahydrofuran, tertiary alcohols such as tert-butanol, and amides such as N,N-dimethylformamide and N,N-dimethylacetoamide. The ratio of methanol and the organic solvent is from 1:3 to 1:10 (v/v).

To a reaction mixture which is obtained by adding the ester (III) and sodium borohydride or lithium borohydride to the organic solvent, methanol is added over 2 to 6 hours with cooling at 0° to 30° C. After the generation of hydrogen gas becomes weak, the reaction mixture undergoes a reaction with stirring, with cooling at 0° to 20° C. for 0.5 to 2 hours and then at room temperature for 1 hour to overnight. Lastly the reaction mixture undergoes a reaction at 40° to 60° C. for 1 to 6 hours with stirring in order to complete the reaction. The reaction can be carried out under any pressure and, usually, is carried out at atmospheric pressure.

The reaction can be also carried out in the same way even if a lower alcohol such as ethanol or propanol is substituted for methanol in the above-mentioned reaction. The produced compound may be purified according to the usual method.

Then, the alcohol (IV) is reacted with a halogenating agent without any solvent or in an organic solvent in the presence or the absence of a base to obtain a halide having the formula (V):

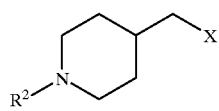

(V)

wherein X and $R^2$ are the same as defined above.

Examples of the halogenating agent are, for instance, thionyl chloride, phosphorus pentachloride, phosphorus tribromide, phosphorus oxychloride and the like. Particularly, the method wherein thionyl chloride is used without adding a base is suitable because the treatment after the reaction can be carried out easily. The amount of the halogenating agent is from 1 to 2 molar equivalents, preferably from 1 to 1.5 molar equivalents, based on the alcohol (IV). In the case of using a base, an organic amine such as pyridine or triethylamine is used.

Examples of the organic solvent to be used are aromatic solvents such as toluene, xylene, benzene and chlorobenzene, halogenated hydrocarbons such as dichloromethane, 1,2-dichloroethane and chloroform, and hydrocarbons such as n-hexane and cyclohexane.

The reaction temperature is suitably determined within the range from 0° C. to the boiling point of the solvent used. The reaction time is from 1 to 24 hours. The reaction can be carried out under any pressure and, usually, is carried out at atmospheric pressure. The produced compound may be purified according to the usual method.

Then, the halide (V) is reacted with a dehydrohalogenating agent in an organic solvent to obtain a methylene compound having the formula (VI):

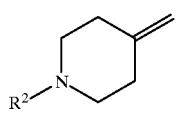

(VI)

wherein $R^2$ is the same as defined above.

The dehydrohalogenating agent is preferably an alkali metal alkoxide such as potassium tert-butoxide, sodium tert-butoxide, sodium methoxide or sodium ethoxide because it has high reactivity and is obtainable at low price. The amount of the dehydrohalogenating agent is from 1 to 5 molar equivalents, preferably from 1 to 4 molar equivalents, based on the halide (V).

The organic solvent to be used is preferably N,N-dimethylformamide, N,N-dimethylacetoamide and dimethylsulfoxide. The reaction time is from 0.5 to 24 hours, preferably from 0.5 to 5 hours. The reaction temperature is from −10° to 100° C., preferably from 0° to 60° C. The reaction can be carried out under any pressure and, usually, is carried out at atmospheric pressure. The produced compound may be purified according to the usual method.

Thereafter, the methylene compound (VI) is hydrolyzed with a strong alkali in water or an organic solvent containing water to obtain 4-methylenepiperidine having the formula (VII):

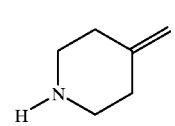

(VII)

Examples of the strong alkali to be used are sodium hydroxide, potassium hydroxide and the like. The amount of the strong alkali is from 1 to 3 molar equivalents based on the methylene compound (VI). The organic solvent to be used is preferably an alcohol having a high boiling point such as ethylene glycol or propylene glycol. The ratio of water and the organic solvent is from 1:20 to 1:1 (v/v).

The reaction temperature is from 80° to 150° C. The reaction time is from 1 to 6 hours. After the reaction, 4-methylenepiperidine is isolated from the reaction mixture by distillation under atmospheric pressure or reduced pressure. The reaction can be carried out under any pressure and, usually, is carried out at atmospheric pressure. The produced compound may be purified according to the usual method.

Thus obtained 4-methylenepiperidine usually has a water content of 20% to 70% by weight. As occasion demands, 4-methylenepiperidine having a water content of at most 20% by weight or anhydrous 4-methylenepiperidine can be also obtained by adding cyclohexane and subjecting the mixture to azeotropic dehydration. Further, a salt thereof with an acid can be also obtained if, for example, the obtained 4-methylenepiperidine is neutralized by adding an acid such as hydrochloric acid or sulfuric acid and then water is removed by distillation In the followings, the processes of the present invention are concretely explained by means of Examples, however, it is not to be understood that the present invention is limited to the Examples. The "%" described in the followings means "% by weight" unless otherwise noted. The reactions were carried out under atmospheric pressure.

EXAMPLE 1

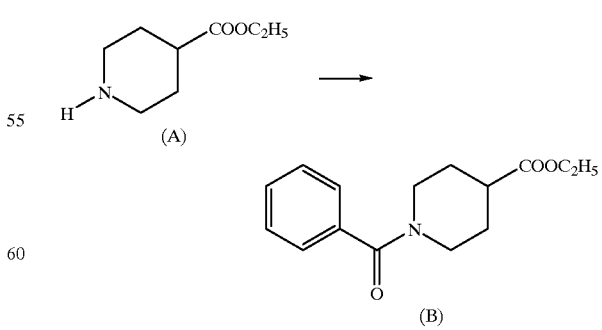

Synthesis of ethyl N-benzoylisonipecotate (B)

To 157.21 g (1 mol) of ethyl isonipecotate (A) were added 79.10 g (1 mol) of pyridine and 1 l of toluene. After cooling the mixture to 9° C., thereto was added dropwise 147.6 g (1.05 mol) of benzoyl chloride at 10° to 20° C. over 30 minutes with cooling. The reaction mixture was further stirred with cooling with ice for 1 hour and at room temperature for 1 hour. Then, thereto was added 500 ml of water to separate an organic layer. The organic layer was washed with 100 ml of water and 200 ml of a 5% aqueous solution of sodium hydrogencarbonate, succesively. Then, thereto was added 10 g of anhydrous magnesium sulfate. After drying, the solvent was removed by distillation to obtain 262.48 g of ethyl N-benzoylisonipecotate (B). The NMR spectrum of the obtained compound was measured. The result is shown below.

NMR(CDCl$_3$)δ: 1.27(3H,t,J=7.2 Hz), 1.5–2.2(4H,br), 2.5–2.65(1H,m), 2.9–3.2(2H,br), 3.6–3.9(1H,br), 4.16(2H, q,J=7.2 Hz), 4.4–4.7(1H,br), 7.40(5H,m)

EXAMPLE 2

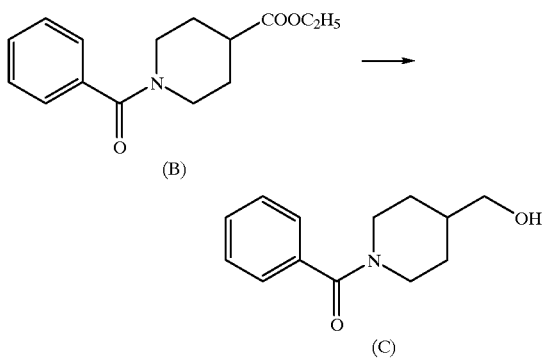

Synthesis of N-benzoyl-4-hydroxymethylpiperidine (C)

To 261.48 g (1 mol) of ethyl N-benzoylisonipecotate (B) obtained in Example 1 was added 800 ml of dioxane and the compound (B) was dissolved. The solution was cooled to 8° C. Thereto was added 75.67 g (2 mol) of sodium borohydride with cooling and, then, added dropwise 243 ml of methanol at 15° to 18° C. over 2 hours with cooling, keeping the reaction mixture not overflowing due to the foaming. The reaction mixture was stirred with cooling at not more than 20° C. for 0.5 hour and at room temperature overnight. Thereafter, the mixture was heated at 45° C. for 6 hours with stirring. After the completion of the reaction, the reaction mixture was cooled down to room temperature and thereto was added 700 ml of iced water and then the mixture was neutralized with 3N hydrochloric acid (400 ml was required). Then, dioxane was removed by distillation under reduced pressure and to the residue were added 200 ml of water and 300 ml of dichloromethane to separate an organic layer. The aqueous layer was extracted twice with 100 ml of dichloromethane. The organic layers were combined and dried over 10 g of anhydrous magnesium sulfate to obtain about 800 ml of a dichloromethane solution containing about 1 mol of N-benzoyl-4-hydroxymethylpiperidine (C). This solution was used in the subsequent stage (Example 3) as it was. A portion of the solution was gathered separately and, after removing the solvent by distillation, the NMR spectrum was measured. The result is shown below. NMR (CDCl$_3$)δ: 1.05–1.35(2H,br), 1.6–1.9(3H,br), 2.5(1H,brs), 2.65–3.1(2H,br), 3.4–3.5(2H,m), 3.65–3.85(1H,br), 4.6–4.9 (1H,br), 7.4(5H,m)

EXAMPLE 3

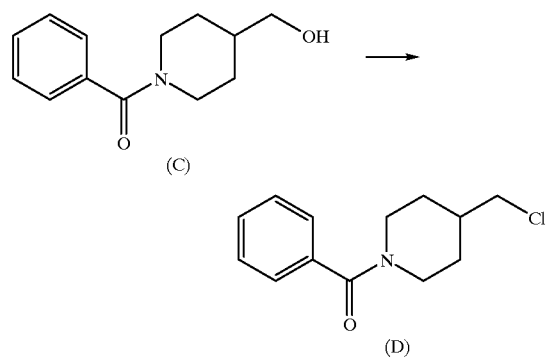

Synthesis of N-benzoyl-4-chloromethylpiperidine (D)

To 800 ml of the dichloromethane solution of N-benzoyl-4-hydroxymethylpiperidine (C) obtained in Example 2, which contains about 1 mol of N-benzoyl-4-hydroxymethylpiperidine, there was added dropwise 109 ml (1.5 mol) of thionyl chloride over 2 hours with keeping the reaction temperature at 25° to 30° C. Then the obtained reaction mixture was stirred at room temperature for 1 hour and at 35° C. for 8 hours. After the completion of the reaction, the solvent and the excess of thionyl chloride were removed by distillation to obtain 248.96 g of N-benzoyl-4-chloromethylpiperidine (D) as a yellowish brown oily matter. The NMR spectrum of the obtained compound was measured. The result is shown below.

NMR(CDCl$_3$)δ: 1.15–1.5(2H,br), 1.7–2.05(3H,br), 2.65–3.15(2H,br), 3.4–3.5(2H,m), 3.7–4.0(1H,br), 4.7–5.0 (1H,br), 7.4(5H,m)

EXAMPLE 4

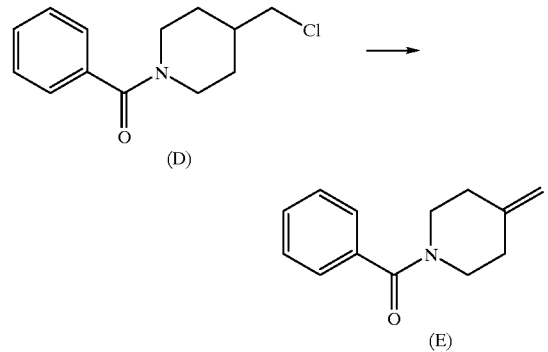

Synthesis of N-benzoyl-4-methylenepiperidine (E)

In 1 l of N,N-dimethylformamide was dissolved 248.96 g (about 1 mol) of N-benzoyl-4-chloromethyl-piperidine (D) obtained in Example 3. The resulting solution was cooled to 5° C. and thereto was added 168.32 g (1.5 mol) of potassium tert-butoxide in five portions at 10° to 20° C. over about 1 hour. After the addition, the mixture was stirred at 10° to 20° C. for 40 minutes. Then, the reaction mixture was poured into a mixed liquid of 500 ml of 1N hydrochloric acid and 500 g of fragmentary ice. Subsequently, thereto was added 200 ml of toluene to separate an organic layer. The aqueous layer was extracted with 200 ml of toluene and the organic layers were combined. The combined organic layer was washed with 500 ml of water. The solvent was removed by distillation under reduced pressure to obtain 193.78 g of N-benzoyl-4-methylenepiperidine (E) as a yellowish brown oily matter. The NMR spectrum of the obtained compound was measured. The result is shown below.

NMR(CDCl$_3$)δ: 2.1–2.45(4H,br), 3.3–3.55(2H,br), 3.65–3.9(2H,br), 4.80(2H,s), 7.4(5H,m),

EXAMPLE 5

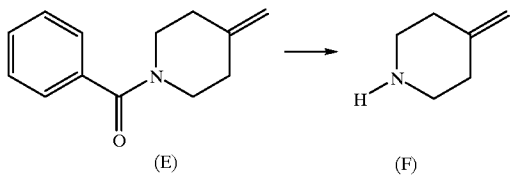

Synthesis of 4-methylenepiperidine (F)

To 193.78 g (about 1 mol) of N-benzoyl-4-methylenepiperidine (E) obtained in Example 4 were added 300 ml of ethylene glycol, 84.17 g (1.5 mol) of potassium hydroxide and 30 ml of water. The resulting mixture was heated at 110° C. for 2 hours with stirring. After the completion of the reaction, thereto was added 170 ml of water. After cooling down to room temperature, thereto was added 150 ml of toluene and the mixture was adjusted to pH 3 with concentrated hydrochloric acid (186 ml was required). The deposited crystal of benzoic acid was separated by filtration. The obtained filtrate was adjusted to pH 4 with a 1N aqueous solution of sodium hydroxide and then water was removed by distillation under reduced pressure. Thereafter, to the residual liquid was added 56 g (1 mol) of potassium hydroxide and the distillation was carried out. The fraction distilled at the boiling point of 97° to 110° C. was collected to obtain 118 g of 4-methylenepiperidine (F). In this distillate, 63% anhydrous 4-methylenepiperidine was contained (calculated by the titration with 0.1 N HCl). The total yield from the isonipecotic acid ethyl ester (A) in Example 1 was 76%. The NMR spectrum of the obtained compound was measured. The result is shown below.

NMR(CDCl$_3$)δ: 2.18(4H,t,J=5.61), 2.86(4H,t,J=5.61), 4.81(2H,s)

EXAMPLE 6

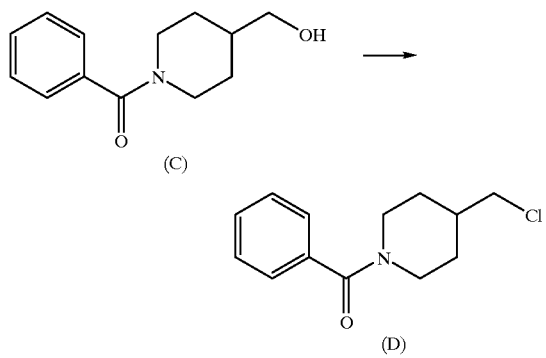

Synthesis of N-benzoyl-4-chloromethylpiperidine (D)

In 10 ml of chloroform was dissolved 2.19 g (10 mmol) of N-benzoyl-4-hydroxymethylpiperidine (C) and to the resulting solution were added 0.81 ml (10 mmol) of pyridine and 1.4 ml (15 mmol) of phosphorus oxychloride. The resulting mixture was stirred at room temperature for 24 hours. After the completion of the reaction, thereto was added 10 ml of chloroform and the resulting mixture was poured into 20 ml of iced water to separate an organic layer. The organic layer was washed with 20 ml of water and dried over 3 g of anhydrous magnesium sulfate. Then, the solvent was removed by distillation to obtain 3.18 g of an oily matter. The oily matter was subjected to silica gel column chromatography (stationary phase: 40 g of Silicagel 60 available from Merck KGaA). The fraction eluted with a hexane/ethyl acetate mixture (1:1 (v/v)) was collected. The solvent was removed by distillation from the obtained fraction to obtain 1.27 g of N-benzoyl-4-chloromethylpiperidine (D) as a colorless crystal. The NMR spectrum of this compound coincided with that of the product in Example 3.

EXAMPLE 7

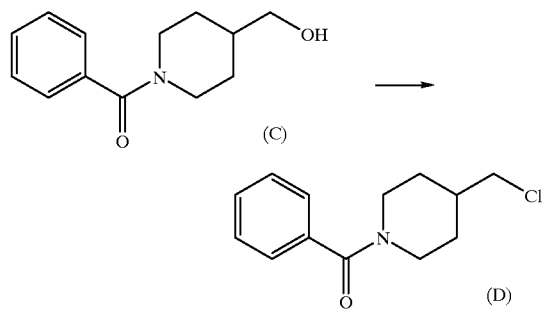

Synthesis of N-benzoyl-4-chloromethylpiperidine (D)

In 20 ml of chloroform was dissolved 2.19 g (10 mmol) of N-benzoyl-4-hydroxymethylpiperidine (C) and to the resulting solution was added 2.08 g (10 mmol) of phosphorus pentachloride. The resulting mixture was stirred at room temperature for 1 hour. After the completion of the reaction, thereto was added 20 ml of chloroform and the resulting mixture was poured into 50 ml of iced water to separate an organic layer. The organic layer was washed with 50 ml of a saturated aqueous solution of sodium hydrogencarbonate and dried over 4 g of anhydrous magnesium sulfate. Then, the solvent was removed by distillation to obtain 3.03 g of an oily matter. The oily matter was subjected to silica gel column chromatography (stationary phase: 50 g of Silicagel 60 available from Merck KGaA). The fraction eluted with a hexane/ethyl acetate mixture (1:1 (v/v)) was collected. The solvent was removed by distillation from the obtained fraction to obtain 1.33 g of N-benzoyl-4-chloromethylpiperidine (D) as a colorless crystal. The NMR spectrum of this compound coincided with that of the product in Example 3.

EXAMPLE 8

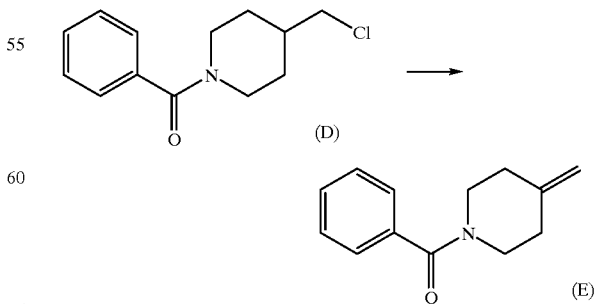

Synthesis of N-benzoyl-4-methylenepiperidine (E)

In 10 ml of N,N-dimethylformamide was dissolved 1.50 g (6.32 mmol) of N-benzoyl-4-chloromethylpiperidine (D). The resulting solution was cooled to 5° C. and thereto was added 1.36 g (25.28 mmol) of sodium methoxide. After stirring at 60° C. for 4 hours, the reaction mixture was cooled down to room temperature and then poured into a mixed liquid of 40 ml of toluene and 40 ml of iced water. An organic layer was separated and dried over 2 g of anhydrous magnesium sulfate and, thereafter, the solvent was removed by distillation. The residual liquid was subjected to silicagel column chromatography (stationary phase: 50 g of Silicagel 60 available from Merck KGaA). The fraction eluted with a hexane/ethyl acetate mixture (2:1 (v/v)) was collected. The solvent was removed by distillation from the obtained fraction to obtain 1.00 g of N-benzoyl-4-methylenepiperidine (E) as a colorless crystal. The NMR spectrum of this compound coincided with that of the product in Example 4.

INDUSTRIAL APPLICABILITY

According to the present invention, 4-methylenepiperidine, an intermediate for synthesizing a fungicide, can be efficiently prepared at low cost in short process.

I claim:

1. A process for preparing a methylene compound having a formula (VI):

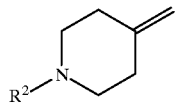

(VI)

wherein $R^2$ is benzoyl group or acetyl group, which comprises reacting a halide having a formula (V):

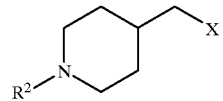

(V)

wherein X is chlorine atom or bromine atom and $R^2$ is the same as defined above, with a dehydrohalogenating agent in an organic solvent.

2. A process for preparing an alcohol having a formula (IV):

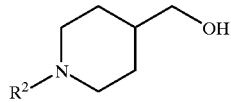

(IV)

wherein $R^2$ is benzoyl group or acetyl group, which comprises reducing an ester having a formula (III):

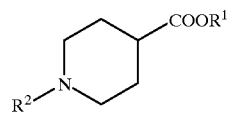

(III)

wherein $R^1$ is methyl group or ethyl group and $R^2$ is the same as defined above, with sodium borohydride or lithium borohydride in an organic solvent containing methanol.

3. A process for preparing a halide having a formula (V):

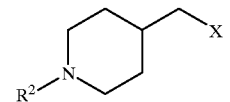

(V)

wherein X is chlorine atom or bromine atom and $R^2$ is benzoyl group or acetyl group, which comprises reacting an alcohol having a formula (IV):

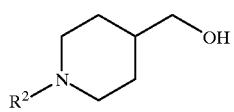

(IV)

wherein $R^2$ is the same as defined above, with a halogenating agent without any solvent or in an organic solvent in the presence or the absence of a base.

4. A process for preparing a methylene compound having a formula (VI):

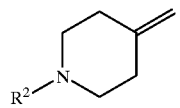

(VI)

wherein $R^2$ is benzoyl group or acetyl group, which comprises reducing an ester having a formula (III):

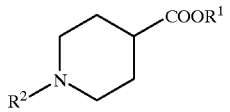

(III)

wherein $R^1$ is methyl group or ethyl group and $R^2$ is the same as defined above, with sodium borohydride or lithium borohydride in an organic solvent containing methanol, reacting a resulting alcohol having a formula (IV):

(IV)

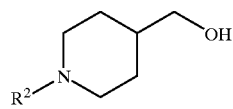

wherein $R^2$ is the same as defined above, with a halogenating agent without any solvent or in an organic solvent in the presence or the absence of a base and reacting a resulting halide having a formula (V):

(V)

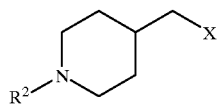

wherein X is chlorine atom or bromine atom and $R^2$ is the same as defined above, with a dehydrohalogenating agent in an organic solvent.

5. A process for preparing an ester having a formula (III):

(III)

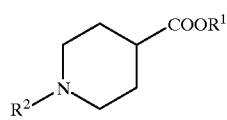

wherein $R^1$ is methyl group or ethyl group and $R^2$ is benzoyl group or acetyl group, which comprises reacting an isonipecotate having a formula (I):

(I)

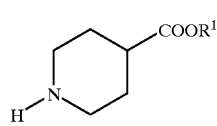

wherein $R^1$ is the same as defined above, with an acylating agent having a formula (II): $R^2X$ or a formula (II'): $(R^2)_2O$ wherein $R^2$ is the same as defined above and X is chlorine atom or bromine atom, in the presence or the absence of a base.

6. A process for preparing 4-methylenepiperidine having a formula (VII):

(VII)

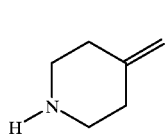

which comprises hydrolyzing a methylene compound having a formula (VI):

(VI)

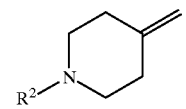

wherein $R^2$ is benzoyl group or acetyl group, with a strong alkali in water or an organic solvent containing water.

7. A process for preparing 4-methylenepiperidine having a formula (VII):

(VII)

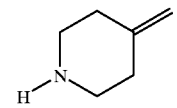

which comprises reacting an isonipecotate having a formula (I):

(I)

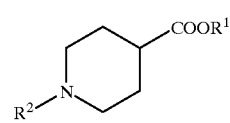

wherein $R^1$ is methyl group or ethyl group, with an acylating agent having a formula (II): $R^2X$ or a formula (II'): $(R^2)_2O$ wherein $R^2$ is benzoyl group or acetyl group and X is chlorine atom or bromine atom, in the presence or the absence of a base, reducing a resulting ester having a formula (III):

(III)

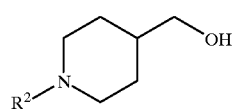

wherein $R^1$ and $R^2$ are the same as defined above, with sodium borohydride or lithium borohydride in an organic solvent containing methanol, reacting a resulting alcohol having a formula (IV):

(IV)

wherein $R^2$ is the same as defined above, with a halogenating agent without any solvent or in an organic solvent in the presence or the absence of a base, reacting a resulting halide having a formula (V):

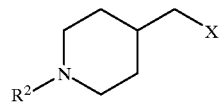 (V)
wherein X and R² are the same as defined above, with a dehydrohalogenating agent in an organic solvent and hydrolyzing a resulting methylene compound having a formula (VI):
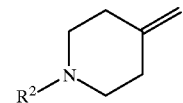 (VI)
wherein R² is the same as defined above, with a strong alkaline in water or an organic solvent containing water.
* * * * *